(12) United States Patent
Ke et al.

(10) Patent No.: US 12,251,428 B2
(45) Date of Patent: Mar. 18, 2025

(54) HYDROGEL COMPOSITION, HYDROGEL BIOMEDICAL MATERIAL, METHOD FOR FACILITATING REGENERATION OF BONE AND MANUFACTURING METHOD OF HYDROGEL COMPOSITION

(71) Applicant: China Medical University, Taichung (TW)

(72) Inventors: Cherng-Jyh Ke, Taichung (TW);
Feng-Huei Lin, Taichung (TW);
Chun-Hsu Yao, Taichung (TW);
Jui-Sheng Sun, Taichung (TW);
Ching-Yun Chen, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 383 days.

(21) Appl. No.: 17/854,229

(22) Filed: Jun. 30, 2022

(65) Prior Publication Data
US 2023/0012279 A1   Jan. 12, 2023

Related U.S. Application Data

(60) Provisional application No. 63/217,377, filed on Jul. 1, 2021.

(51) Int. Cl.
*A61K 38/45* (2006.01)
*A61K 9/00* (2006.01)
(Continued)

(52) U.S. Cl.
CPC ............ *A61K 38/45* (2013.01); *A61K 9/0024* (2013.01); *A61K 9/06* (2013.01); *A61K 31/728* (2013.01);
(Continued)

(58) Field of Classification Search
CPC ........ A61K 38/45; A61K 9/0024; A61K 9/06; A61K 31/728; A61K 31/16; A61K 35/19;
(Continued)

(56) References Cited

U.S. PATENT DOCUMENTS 4,743,229 A   5/1988   Chu

FOREIGN PATENT DOCUMENTS

WO   2021055703 A1   3/2021

OTHER PUBLICATIONS

Wang et al, Hybrid Hydrogel Composed of Hyaluronic Acid, Gelatin, Extracellular Cartilage Matrix for Perforated TM, Repair, Frontiers in Bioengineering and Biotechnology. (Year: 2021).*

* cited by examiner

*Primary Examiner* — Carlos A Azpuru

(57) ABSTRACT

A hydrogel composition, a hydrogel biomedical material, a method for facilitating regeneration of a bone and a manufacturing method of a hydrogel composition are provided. The hydrogel composition includes a first deionized water, a gel powder, a transglutaminase mixture and a hyaluronic acid powder. The gel powder includes gelatin and alginic acid. The first deionized water, the gel powder, the transglutaminase mixture and the hyaluronic acid powder are evenly mixed. Based on the hydrogel composition being 100 wt %, the first deionized water is 95 wt % to 98.46 wt %, the gel powder is 1 wt % to 3 wt %, the transglutaminase mixture is 0.04 wt % to 0.15 wt %, and the hyaluronic acid powder is 0.5 wt % to 1.5 wt %.

3 Claims, 10 Drawing Sheets
(2 of 10 Drawing Sheet(s) Filed in Color)

(51) Int. Cl.
*A61K 9/06* (2006.01)
*A61K 31/728* (2006.01)
*A61K 35/16* (2015.01)
*A61K 35/19* (2015.01)
*A61K 38/36* (2006.01)
*A61K 47/02* (2006.01)
*A61K 47/18* (2017.01)
*A61K 47/34* (2017.01)
*A61K 47/36* (2006.01)
*A61K 47/42* (2017.01)
*A61K 47/69* (2017.01)

(52) U.S. Cl.
CPC ............. *A61K 35/16* (2013.01); *A61K 35/19* (2013.01); *A61K 38/36* (2013.01); *A61K 47/02* (2013.01); *A61K 47/183* (2013.01); *A61K 47/34* (2013.01); *A61K 47/36* (2013.01); *A61K 47/42* (2013.01); *A61K 47/6903* (2017.08)

(58) Field of Classification Search
CPC ...... A61K 38/36; A61K 47/02; A61K 47/183; A61K 47/34; A61K 47/35; A61K 47/42; A61K 47/6903
See application file for complete search history.

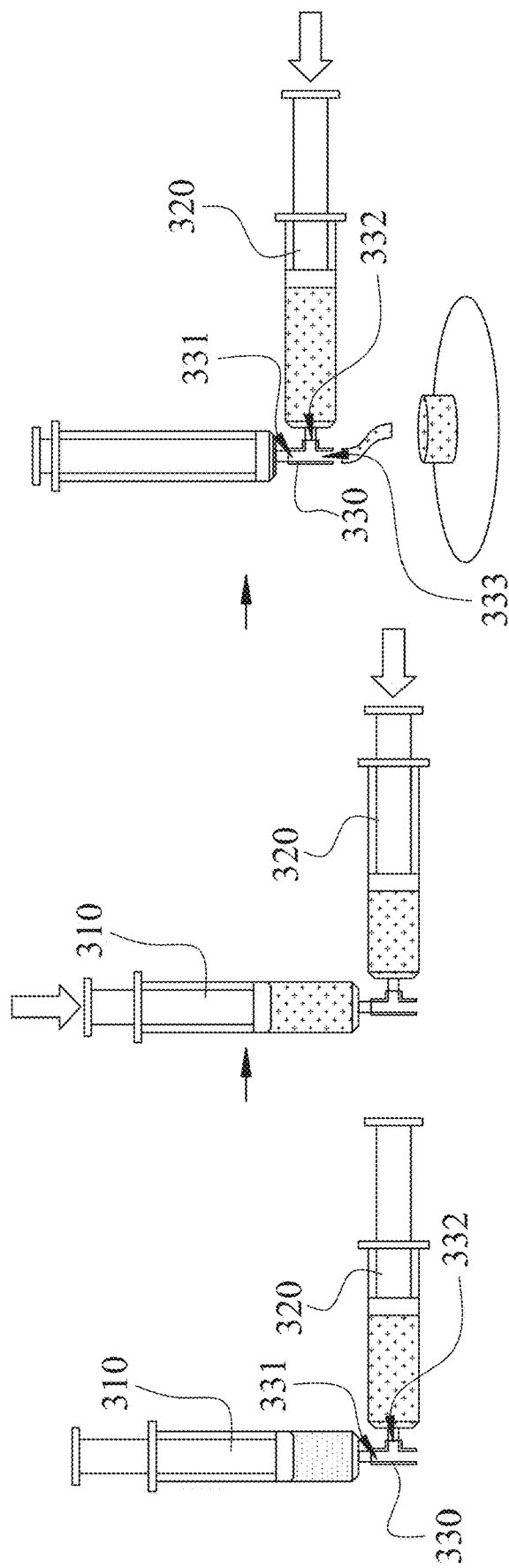

HYDROGEL COMPOSITION, HYDROGEL BIOMEDICAL MATERIAL, METHOD FOR FACILITATING REGENERATION OF BONE AND MANUFACTURING METHOD OF HYDROGEL COMPOSITION

RELATED APPLICATIONS

This application claims priority to U.S. Provisional Application Ser. No. 63/217,377, filed Jul. 01, 2021, which is herein incorporated by reference.

BACKGROUND

Technical Field

The present disclosure relates to a hydrogel composition and a hydrogel biomedical material. More particularly, the present disclosure relates to a hydrogel composition and a hydrogel biomedical material which facilitate bone healing.

Description of Related Art

Human bones are made of organic materials and inorganic materials. Organic materials are mainly bone collagen fibers and mucoprotein, and organic materials are about 30% to 40% of the total weight of adult dry bone. Inorganic materials are mainly calcium phosphate, calcium carbonate and calcium fluoride, and inorganic materials are about 60% to 70% of the total weight of dry bone. The overall elasticity and hardness of bones are decided by the ratio of bone collagen fibers and calcium phosphate, and the aforementioned ratio will change with age. Inorganic materials in human bones increase as aging, and organic materials therein decrease relatively. Therefore, the elders' bones are brittle, fragile and difficult to heal.

As the population ages, people's attention is drawn to bone-related and joint-related problems caused by aging. Degenerative arthritis is the most common problem caused by aging, and over half of the elders are suffering from degenerative arthritis according to the statistics. Degenerative arthritis patients can be treated according to the degree of joints wearing away and inflammation. For mild degenerative arthritis, patients can be treated by taking medicines, resting, physical therapy, arthroscopic lavage or high tibial osteotomy.

Patients with severely eroded joints should consider an implantation of joint prosthesis because the joints thereof cannot support their weights anymore. However, problems such as poor healing between bones and bone grafts (for example, cartilage, autograft, allograft, synthetic bone graft or nail), low osseointegration and osteomyelitis often happen after these invasive procedures.

In this regard, scientists and manufacturers are pursuing the goal of developing a biomedical material which facilitates bone healing.

SUMMARY

According to one aspect of the present disclosure, a hydrogel composition includes a first deionized water, a gel powder, a transglutaminase mixture and a hyaluronic acid powder. The gel powder includes gelatin and alginic acid. The first deionized water, the gel powder, the transglutaminase mixture and the hyaluronic acid powder are evenly mixed. Based on the hydrogel composition being 100 wt %, the first deionized water is 95 wt % to 98.46 wt %, the gel powder is 1 wt % to 3 wt %, the transglutaminase mixture is 0.04 wt % to 0.15 wt %, and the hyaluronic acid powder is 0.5 wt % to 1.5 wt %.

According to another aspect of the present disclosure, a hydrogel biomedical material includes the hydrogel composition of the aforementioned aspect and an additive. The additive and the hydrogel composition are evenly mixed, and the additive is selected from the group consisting of a growth factor, a platelet-rich plasma, a platelet-rich fibrin and an antibiotic.

According to one another aspect of the present disclosure, a method for facilitating a regeneration of a bone includes placing the hydrogel biomedical material of the aforementioned aspect between a bone graft and the bone which is to be regenerated.

According to still another aspect of the present disclosure, a manufacturing method of a hydrogel composition includes the steps as follows. A first deionized water is provided in a first syringe, a gel powder, a transglutaminase mixture and a hyaluronic acid powder are provided in a second syringe, an assembling step is performed, and a mixing step is performed. In the assembling step, the first syringe is connected to a first opening of a three-way valve and the second syringe is connected to a second opening of the three-way valve, and a ball of the three-way valve is turned to make the first opening be communicated with the second opening. In the mixing step, by pushing a plunger of the first syringe and a plunger of the second syringe, the first deionized water, the gel powder, the transglutaminase mixture and the hyaluronic acid powder are evenly mixed in the second syringe, so as to form a hydrogel composition after crosslinking. The gel powder includes gelatin and alginic acid. Based on the hydrogel composition being 100 wt %, the first deionized water is 95 wt % to 98.46 wt %, the gel powder is 1 wt % to 3 wt %, the transglutaminase mixture is 0.04 wt % to 0.15 wt %, and the hyaluronic acid powder is 0.5 wt % to 1.5 wt %.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows:

FIG. 3A is a schematic view of Step 130 and Step 230 of the manufacturing method of the hydrogel composition according to FIG. 1 and FIG. 2.

FIG. 3B is a schematic view of Step 140 and Step 240 of the manufacturing method of the hydrogel composition according to FIG. 1 and FIG. 2.

FIG. 3C is a schematic view of Step 250 of the manufacturing method of the hydrogel composition according to FIG. 2.

DETAILED DESCRIPTION

Figure 1:
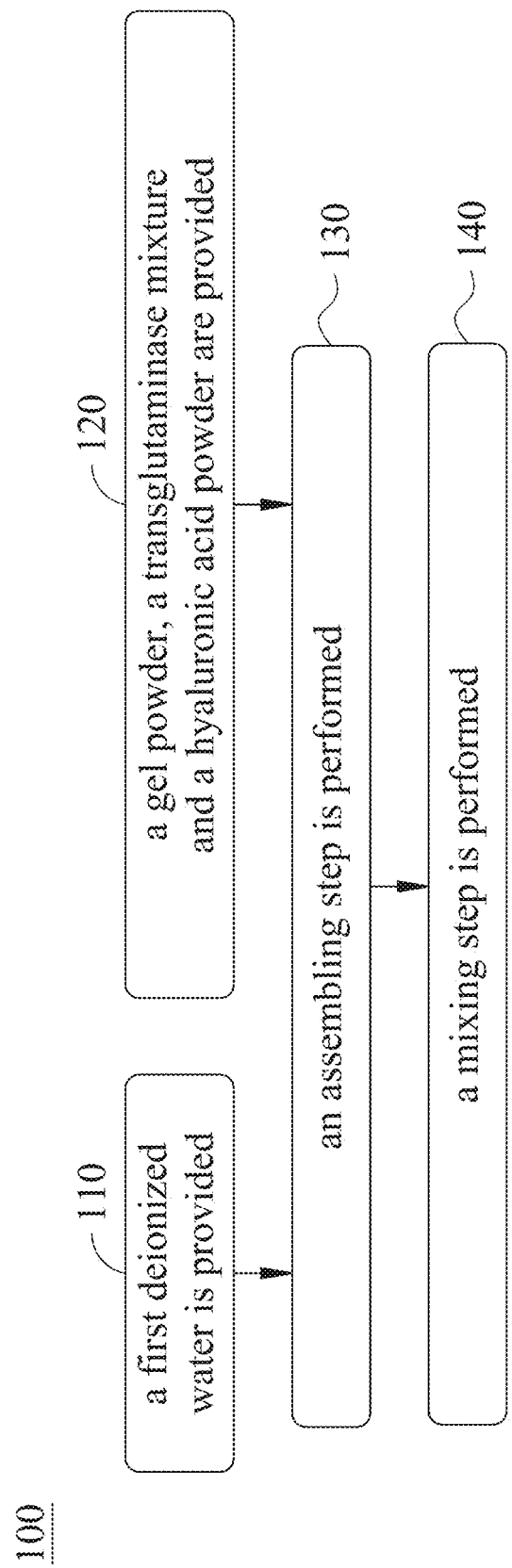
FIG. 1 is a flow chart of a manufacturing method of a hydrogel composition according to one embodiment of the present disclosure.

The present disclosure will be further exemplified by the following specific embodiments. However, the embodiments can be applied to various inventive concepts and can be embodied in various specific ranges. The specific embodiments are only for the purposes of description, and are not limited to these practical details thereof. Furthermore, in order to simplify the drawings, some conventional structures and elements will be illustrated in the drawings by a simple and schematic way.

According to one embodiment of one aspect of the present disclosure, a hydrogel composition includes a first deionized water, a gel powder, a transglutaminase mixture and a hyaluronic acid powder. The gel powder includes gelatin and alginic acid. The first deionized water, the gel powder, the transglutaminase mixture and the hyaluronic acid powder are evenly mixed.

Based on the hydrogel composition being 100 wt %, the first deionized water is 95 wt % to 98.46 wt %, the gel powder is 1 wt % to 3 wt %, the transglutaminase mixture is 0.04 wt % to 0.15 wt %, and the hyaluronic acid powder is 0.5 wt % to 1.5 wt %. By using the abovementioned materials with particular ratios, the hydrogel composition with high biocompatibility can be manufactured. The hydrogel composition is able to carry growth factors, cytokines, antibiotics or other chemicals. When the hydrogel composition is further applied to bone implantations, problems such as poor healing between bones and bone grafts, low osseointegration and osteomyelitis can be effectively improved.

The transglutaminase mixture can be made of a transglutaminase powder, a phosphate buffered saline, ethylenediaminetetraacetic acid and a second deionized water through a freeze-drying process. The aforementioned freeze-drying process can include the steps such as cooling, drying and cutting, which makes the transglutaminase mixture into powder. Therefore, high-temperature is unnecessary in the drying process, and the activity of transglutaminase can remain.

According to one embodiment of another aspect of the present disclosure, a hydrogel biomedical material includes the hydrogel composition of the aforementioned aspect and an additive. The additive and the hydrogel composition are evenly mixed, and the additive is selected from the group consisting of a growth factor, a platelet-rich plasma, a platelet-rich fibrin and an antibiotic. The additive has the ability of stimulating cell proliferation and cell differentiation, which helps the healing of bone implantation, periosteum growth and bone calcification. Furthermore, the additive can also kill the pathogens at the bone implantation, so as to prevent the wound from infection which slows down the healing of the wound. The additive of the present disclosure can be any types of chemical compositions or biomaterials which improves the healing of bone tissue. The additive of the present disclosure is not limited to the aforementioned materials.

According to one embodiment of one another aspect of the present disclosure, a method for facilitating a regeneration of a bone includes placing the hydrogel biomedical material of the aforementioned aspect between a bone graft and the bone which is to be regenerated. For example, the bone graft can be cartilage, autograft, allograft, synthetic bone graft, nail, etc. The bone graft can be first wrapped by the hydrogel biomedical material, and the hydrogel biomedical material and the bone graft can be implanted to the bone which is to be regenerated together. Also, the hydrogel biomedical material can be injected between the bone graft and the surrounding tissue after the bone graft is implanted. However, the method of placing the hydrogel biomedical material should be adjusted according to the condition of the bone to be regenerated and the implantation of the bone graft, so the present disclosure is not limited to the aforementioned methods of placing the hydrogel biomedical material.

In this regard, the hydrogel biomedical material can reduce an inflammatory response of the bone as regenerating, or facilitate the regeneration of the bone around the bone graft.

Figure 2:
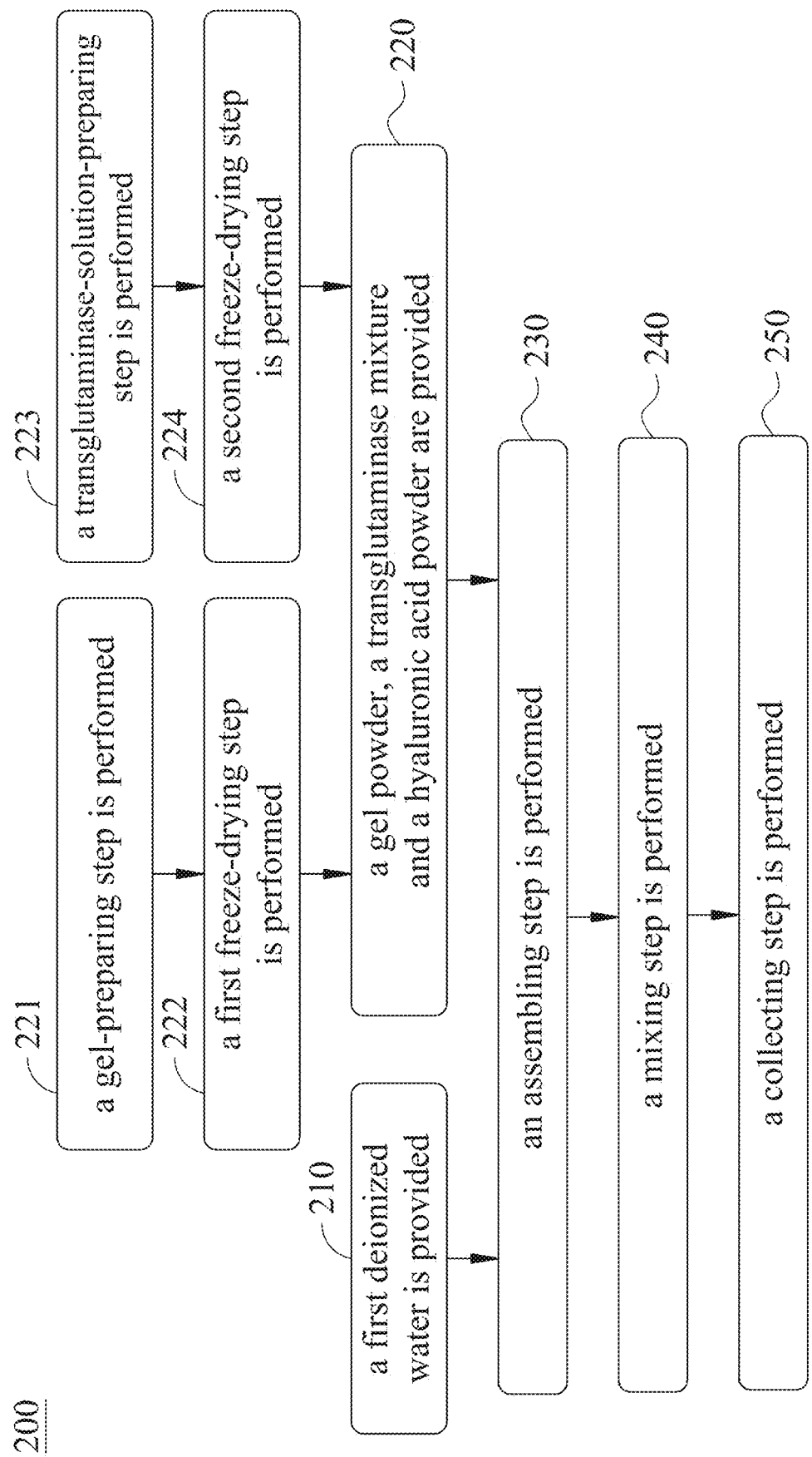
FIG. 2 is a flow chart of the manufacturing method of the hydrogel composition according to another embodiment of the present disclosure.

Please refer to FIG. 1, FIG. 2, FIG. 3A and FIG. 3B. FIG. 1 is a flow chart of a manufacturing method of a hydrogel composition 100 according to one embodiment of the present disclosure. FIG. 2 is a flow chart of the manufacturing method of the hydrogel composition 200 according to another embodiment of the present disclosure. FIG. 3A is a schematic view of Step 130 and Step 230 of the manufacturing method of the hydrogel composition 100, 200 according to FIG. 1 and FIG. 2. FIG. 3B is a schematic view of Step 140 and Step 240 of the manufacturing method of the hydrogel composition 100, 200 according to FIG. 1 and FIG. 2. According to one embodiment of still another aspect of the present disclosure, the manufacturing method of the hydrogel composition 100 includes Step 110, Step 120, Step 130 and Step 140.

In Step 110, a first deionized water is provided, and the first deionized water is contained in a first syringe 310.

In Step 120, a gel powder, a transglutaminase mixture and a hyaluronic acid powder are provided, and the gel powder, the transglutaminase mixture and the hyaluronic acid powder are contained in a second syringe 320. The compositions or ratios of the first deionized water, the gel powder, the transglutaminase mixture and the hyaluronic acid powder are the same as the hydrogel composition of the aforementioned aspect, and the details will not be repeated herein.

In Step 130, an assembling step is performed by connecting the first syringe 310 to a first opening 331 of a three-way valve 330 and connecting the second syringe 320 to a second opening 332 of the three-way valve 330, and a ball (not illustrated) of the three-way valve 330 is turned to make the first opening 331 be communicated with the second opening 332.

In Step 140, a mixing step is performed by pushing a plunger of the first syringe 310 and a plunger of the second syringe 320 to evenly mix the first deionized water, the gel powder, the transglutaminase mixture and the hyaluronic acid powder in the second syringe 320, so as to form a hydrogel composition after crosslinking. In the mixing step, the plunger of the first syringe 310 and the plunger of the second syringe 320 can be pushed alternately, so as to sufficiently mix the aforementioned materials to obtain the hydrogel composition with more uniform crosslink degree.

Moreover, please refer to FIG. 2, FIG. 3A to FIG. 3C. FIG. 3C is a schematic view of Step 250 of the manufacturing method of the hydrogel composition 200 according to FIG. 2. The manufacturing method of the hydrogel composition 200 of the present embodiment includes Step 210, Step 220, Step 221, Step 222, Step 223, Step 224, Step 230, Step 240 and Step 250.

Step 210 is to provide a first deionized water, Step 220 is to provide a gel powder, a transglutaminase mixture and a hyaluronic acid powder, Step 230 is to perform an assembling step and Step 240 is to perform a mixing step. Step 210, Step 220, Step 230 and Step 240 of the present embodiment are respectively the same as Step 110, Step 120, Step 130 and Step 140 of the aforementioned embodiment, and the details will not be repeated herein.

In Step 221, a gel-preparing step is performed by mixing the gelatin, the alginic acid and a third deionized water, so as to form a gel.

In Step 222, a first freeze-drying step is performed by freeze-drying the gel to form the gel powder. That is, the gel is freeze-dried to remove the water therein and is cut to form the gel powder. Therefore, high-temperature is unnecessary in the drying process, and the structures of the gelatin and the alginic acid in the gel can remain.

In Step 223, a transglutaminase-solution-preparing step is performed by mixing a transglutaminase powder, a phosphate buffered saline, ethylenediaminetetraacetic acid and a second deionized water, so as to form a transglutaminase solution.

In Step 224, a second freeze-drying step is performed by freeze-drying the transglutaminase solution to form the transglutaminase mixture. The aforementioned freeze-drying process can include the steps such as cooling, drying and cutting, which makes the transglutaminase mixture into powder. Therefore, high-temperature is unnecessary in the drying process, and the activity of transglutaminase can remain.

In Step 250, a collecting step is performed by turning the ball of the three-way valve 330 to make the second opening 332 be communicated with a third opening 333 of the three-way valve 330, wherein the plunger of the second syringe 320 is pushed to expel the hydrogel composition through the third opening 333 for further collection and application.

In the following paragraphs, the hydrogel composition and the hydrogel biomedical material of the present disclosure are tested to understand the material properties, biocompatibilities and effects on bone healing thereof.

<Cell Culture>

In the present experiment, cells are cultured on the hydrogel compositions of the 1st comparative example, the 1st example and the 2nd example. The hydrogel composition of the 1st comparative example only includes the first deionized water and the gel powder. The hydrogel compositions of the 1st example and the 2nd example includes the first deionized water, the gel powder, the transglutaminase mixture and the hyaluronic acid powder. The actual compositions of the hydrogel compositions of the 1st comparative example, the 1st example and the 2nd example are listed in Table 1 below.

TABLE 1

|  | 1st Comparative Example | 1st Example | 2nd Example |
|---|---|---|---|
| First Deionized Water (mL) | 4 | 4 | 4 |
| Gel Powder (g) | 0.075 | 0.075 | 0.075 |
| Transglutaminase Mixture (g) | — | 0.002 | 0.004 |
| Hyaluronic Acid Powder (g) | — | 0.04 | 0.04 |

Figure 4A:
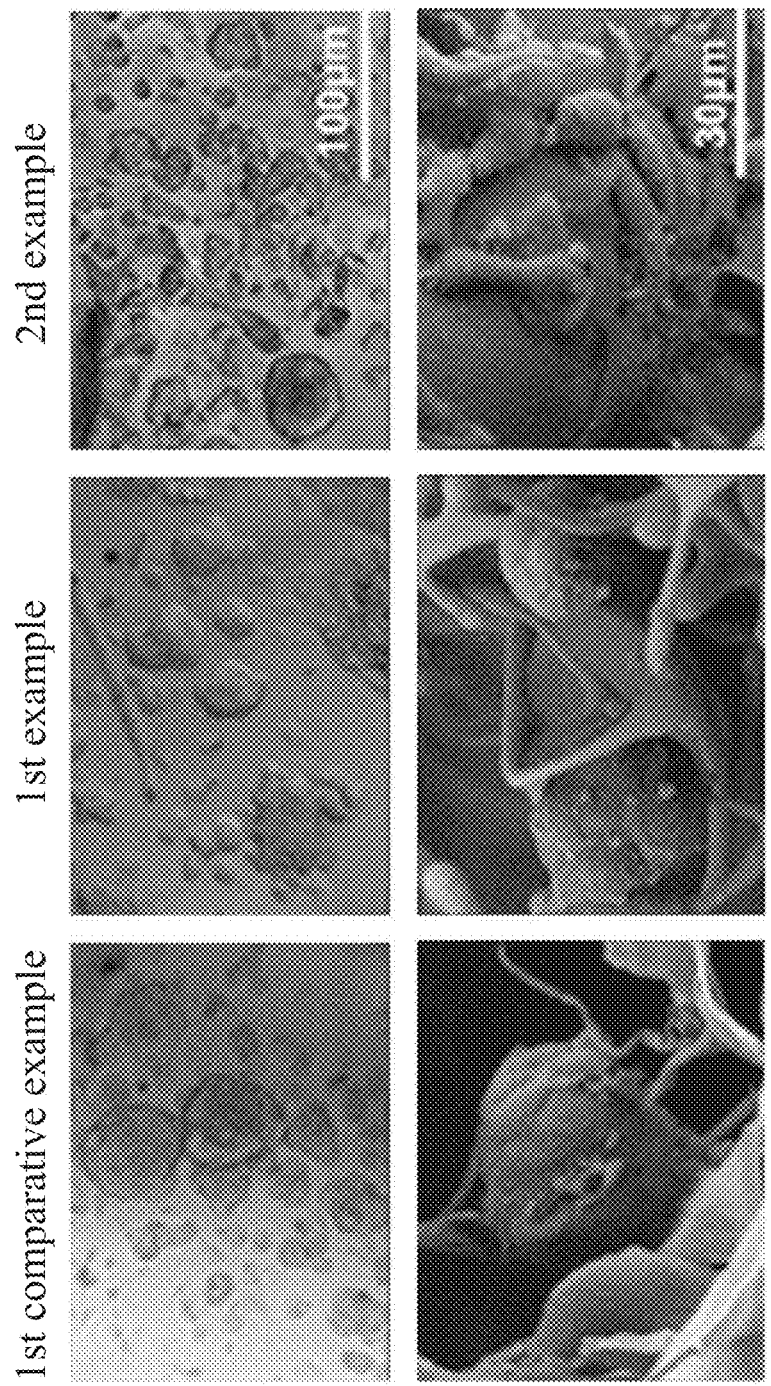
FIG. 4A shows scanning electron microscopic images of cell culture results of the hydrogel compositions of the 1st comparative example, the 1st example and the 2nd example.
Figure 4B:
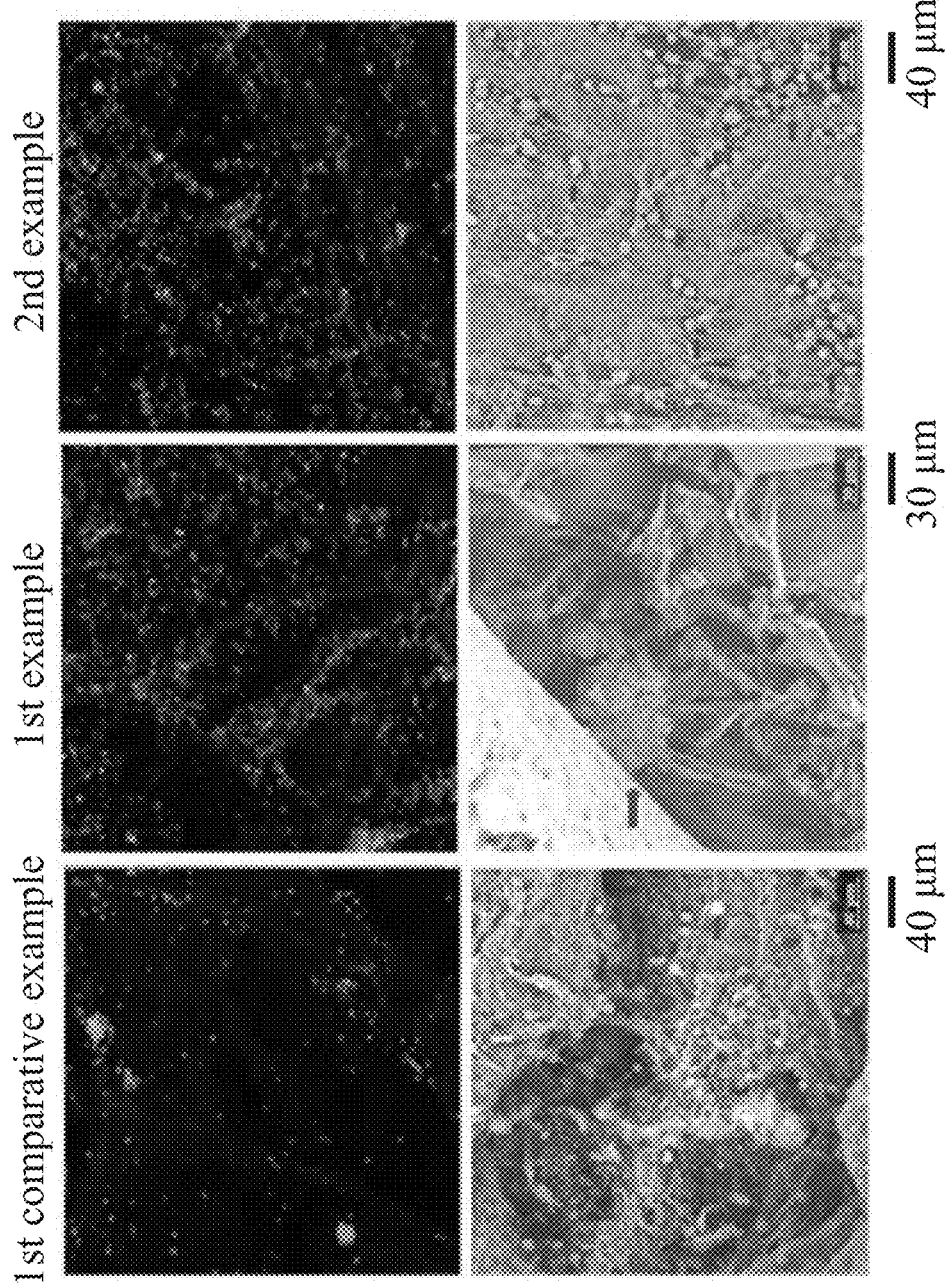
FIG. 4B shows fluorescent microscope images of Live/Dead cell staining test and scanning electron microscopic images of cell culture results of the hydrogel compositions of the 1st comparative example, the 1st example and the 2nd example.

In the present experiment, human osteosarcoma cells (MG63 cells) are cultured on the hydrogel compositions of the 1st comparative example, the 1st example and the 2nd example for 7 days and then observed. Please refer to FIG. 4A and FIG. 4B. FIG. 4A shows scanning electron microscopic images of cell culture results of the hydrogel compositions of the 1st comparative example, the 1st example and the 2nd example. FIG. 4B shows fluorescent microscope images of Live/Dead cell staining test and scanning electron microscopic images of cell culture results of the hydrogel compositions of the 1st comparative example, the 1st example and the 2nd example. From FIG. 4A and FIG. 4B, it can be observed that the MG63 cells attach to the hydrogel compositions of the 1st example and the 2nd example well, and the cell adhesions thereof are significantly better than the hydrogel composition of the 1st comparative example. Furthermore, the cell adhesion of the hydrogel composition of the 2nd example is the best.

<Activity of Alkaline Phosphatase>

In the present experiment, the activities of alkaline phosphatase (ALP) of the hydrogel compositions of the 1st comparative example, the 1st example and the 2nd example are tested. The activity of ALP can be tested by colorimetric method or continuous monitoring method. In colorimetric method, ALP can hydrolyze disodium phenyl phosphate under basic conditions, so as to form phosphoric acid and free phenol. The free phenol can react with 4-aminoantipyrine and become red quinone after oxidized by potassium ferricyanide. The intensity of color is directly proportional to the activity of ALP. In the continuous monitoring method, ALP can make 4-nitrophenyl phosphate (4-NPP) release acyl phosphate under basic conditions. Then, 2-amino-2-methyl-1-propanol (AMP) participates in the transfer of acyl phosphate and enhances the reaction rate of ALP. The free 4-nitrophenol (4-NP) and yellow quinone are formed. The increasing rate of absorbance thereof is directly proportional to the activity of ALP.

Figure 5:
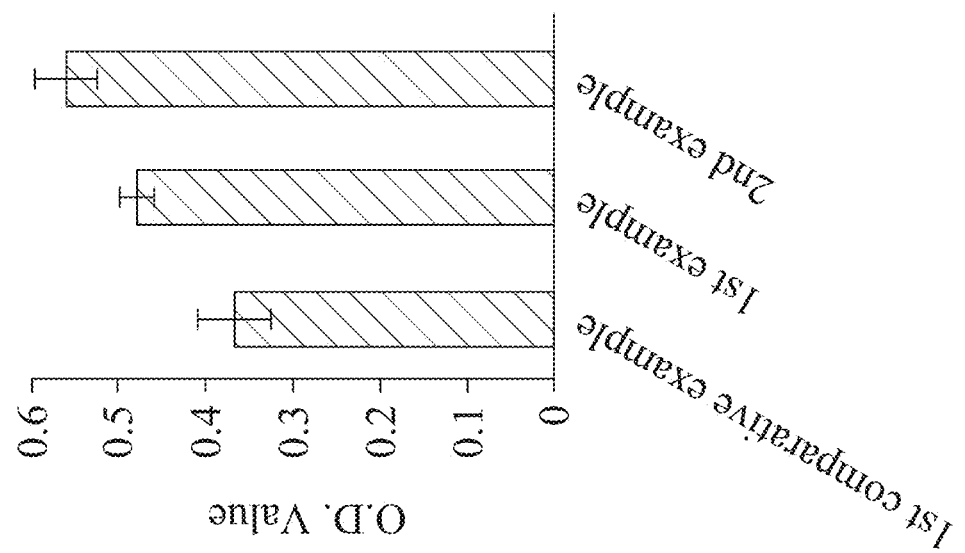
FIG. 5 is an analysis diagram of alkaline phosphatase activity of the hydrogel compositions of the 1st comparative example, the 1st example and the 2nd example.

Please be noted that, the activity of ALP would increase as the bone heals. Thus, higher activity of ALP represents better bone mineralization, which helps bone healing. Please refer to FIG. 5, which is an analysis diagram of alkaline phosphatase activity of the hydrogel compositions of the 1st comparative example, the 1st example and the 2nd example. In FIG. 5, the activities of ALP of the 1st example and the 2nd example are both higher than the 1st comparative example, which proves that the hydrogel composition of the present disclosure has high activity of ALP and is able to improve bone healing.

<Ability of Releasing Additive>

In the present experiment, the releasing abilities of the hydrogel biomedical materials of the 2nd comparative example, the 3rd example and the 4th example are tested. The hydrogel biomedical materials of the 2nd comparative example, the 3rd example and the 4th example are obtained by adding vancomycin into the hydrogel compositions of the 1st comparative example, the 1st example and the 2nd example, respectively. In the present experiment, the hydrogel biomedical materials of the 2nd comparative example, the 3rd example and the 4th example are placed in a phosphate buffered saline (PBS) including $H_2O_2$, and the released amounts of vancomycin at different points of time under a 37° C. environment are observed to understand the ability of controlling releasing of each hydrogel biomedical material.

Figure 6:
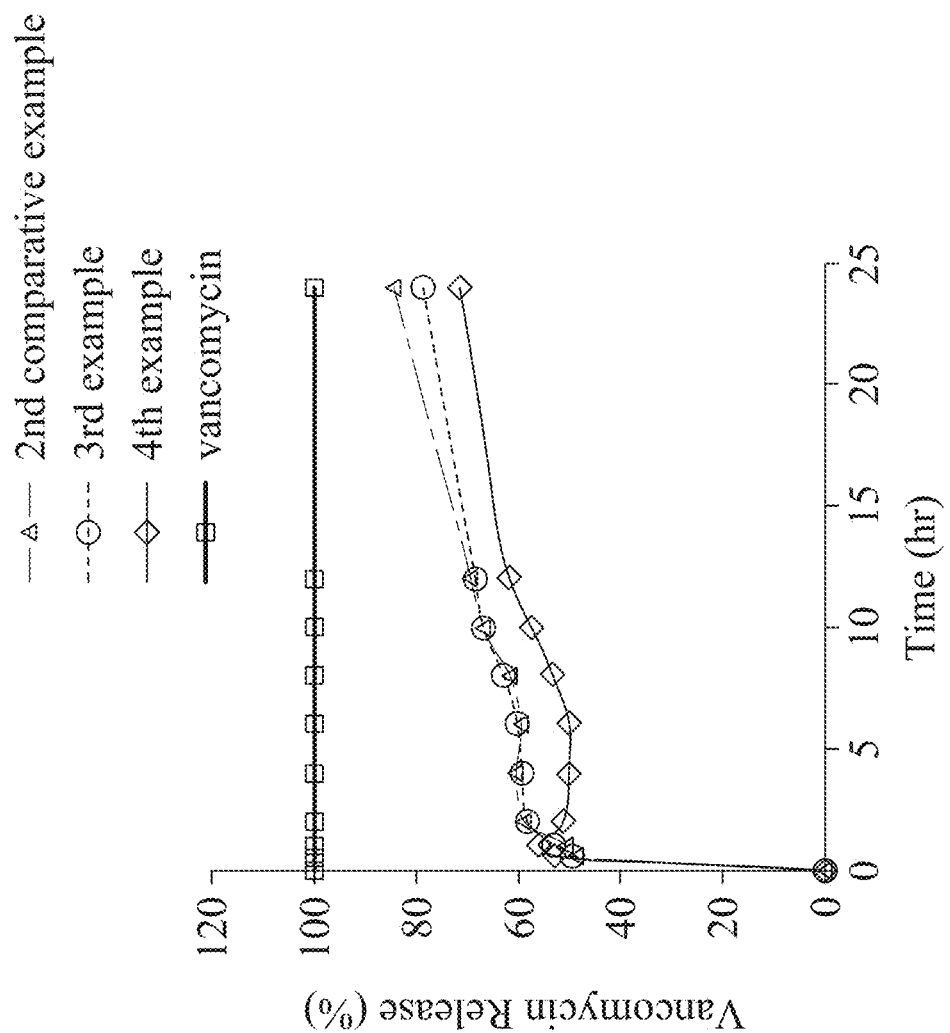
FIG. 6 is an analysis diagram of vancomycin release of the hydrogel biomedical materials of the 2nd comparative example, the 3rd example and the 4th example.

Please refer to FIG. 6, which is an analysis diagram of vancomycin release of the hydrogel biomedical materials of the 2nd comparative example, the 3rd example and the 4th example. In FIG. 6, the releasing rate of vancomycin from the hydrogel biomedical material of the 4th example is lower, so that the release of the additive can be controlled for a long time.

<Bone Healing>

In the present experiment, the hydrogel biomedical materials of the 2nd comparative example, the 3rd example and the 4th example are administered to rat animal models, and the bone healing processes thereof are observed. The rat animal models of the present experiment are the rat animal models with osteomyelitis.

Figure 7B:
FIG. 7A, FIG. 7B, FIG. 7C and FIG. 7D show immunohistochemistry images of rat osteomyelitis animal models which are untreated and treated by administering the hydrogel biomedical materials of the 2nd comparative example, the 3rd example and the 4th example thereto, respectively.
Figure 7D:
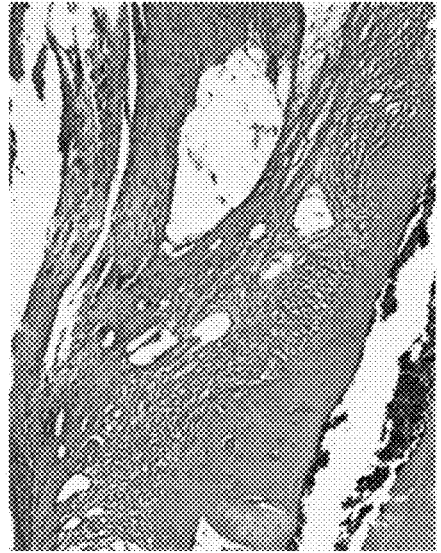
Figure 7A:
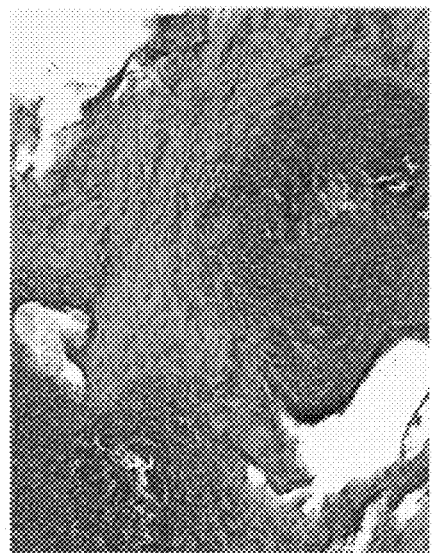
Figure 7C:

Please refer to FIG. 7A to FIG. 7D. FIG. 7A, FIG. 7B, FIG. 7C and FIG. 7D show immunohistochemistry images of rat osteomyelitis animal models which are untreated and treated by administering the hydrogel biomedical materials of the 2nd comparative example, the 3rd example and the 4th example thereto, respectively. FIG. 7A is a biopsy from the infection portion of the untreated rat animal model. FIG. 7B, FIG. 7C and FIG. 7D are biopsies from the infection portions of the rat animal models which are treated with the hydrogel biomedical materials of the 2nd comparative example, the 3rd example and the 4th example, respectively. From FIG. 7A and FIG. 7B, the conditions of the bones which are untreated and treated with the hydrogel biomedical material of the 2nd comparative example are similar, which means the recovery is poor after treated with the hydrogel biomedical material of the 2nd comparative example. From FIG. 7C and FIG. 7D, the bone structures become more intact after treated with the hydrogel biomedical materials of the 3rd example and the 4th example, which means the hydrogel biomedical material of the present disclosure can effectively improve bone healing.

<Crosslinking Reaction>

In the present experiment, the crosslink degrees of the hydrogel compositions of the 1st comparative example, the 1st example and the 2nd example and the hydrogel biomedical materials of the 2nd comparative example, the 3rd example and the 4th example are compared, so as to understand whether the crosslink rates of the hydrogel compositions and the hydrogel biomedical materials would be affected by the different compositions thereof or not.

Figure 8:
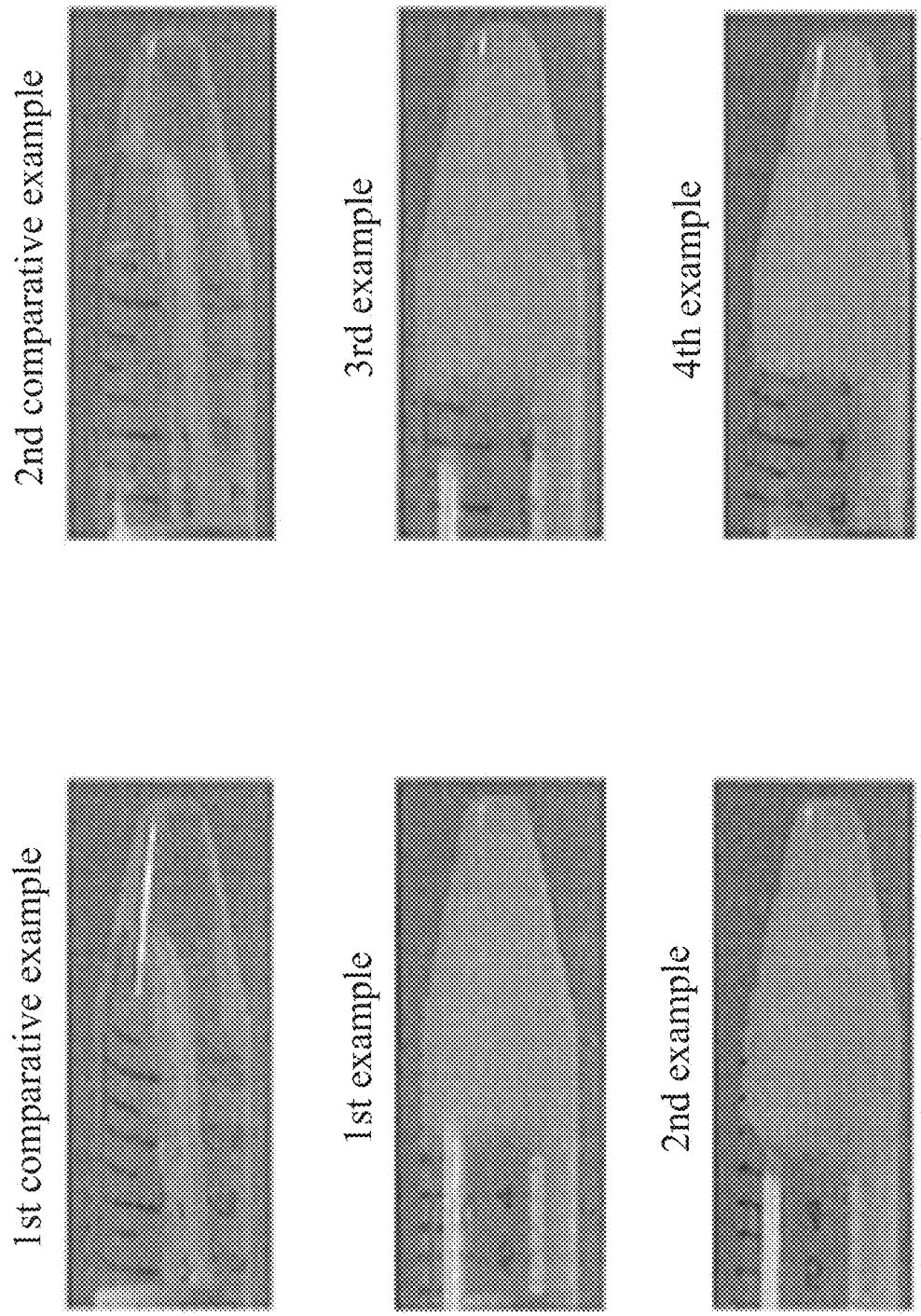
FIG. 8 shows images of crosslink degrees of the hydrogel compositions of the 1st comparative example, the 1st example and the 2nd example and the hydrogel biomedical materials of the 2nd comparative example, the 3rd example and the 4th example.

First, please refer to FIG. 8, which shows images of crosslink degrees of the hydrogel compositions of the 1st comparative example, the 1st example and the 2nd example and the hydrogel biomedical materials of the 2nd comparative example, the 3rd example and the 4th example. In FIG. 8, at the same time, the hydrogel compositions of the 1st example and the 2nd example and the hydrogel biomedical materials of the 3rd example and the 4th example are all crosslinked and turn into a gel form (the opaque substances in the ends of tubes in FIG. 8), but the hydrogel composition of the 1st comparative example and the hydrogel biomedical material of the 2nd comparative example are still liquid (the transparent liquid in the ends of tubes in FIG. 8). It means that the crosslink degrees of the 1st example to the 4th example are significantly higher than that of the 1st comparative example and the 2nd comparative example after the same crosslink time.

Figure 9:
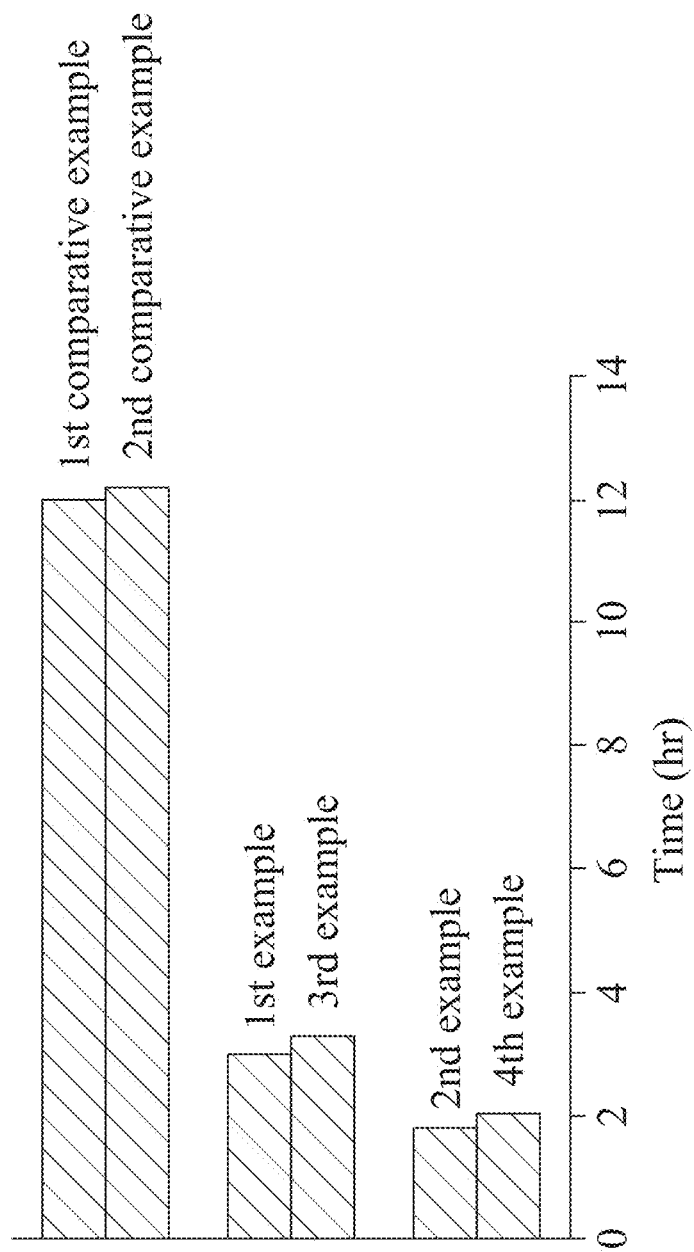
FIG. 9 is an analysis diagram of crosslink time of the hydrogel compositions of the 1st comparative example, the 1st example and the 2nd example and the hydrogel biomedical materials of the 2nd comparative example, the 3rd example and the 4th example.

Please refer to FIG. 9, which is an analysis diagram of crosslink time of the hydrogel compositions of the 1st comparative example, the 1st example and the 2nd example and the hydrogel biomedical materials of the 2nd comparative example, the 3rd example and the 4th example. In FIG. 9, it is more obvious that the crosslink time of the hydrogel composition of the 1st comparative example and the hydrogel biomedical material of the 2nd comparative example is about 12 hours, which is significantly longer than the crosslink time of the hydrogel compositions of the 1st example and the 2nd example and the hydrogel biomedical materials of the 3rd example and the 4th example (about 2-4 hours). Also, in FIG. 9, the crosslink time of the hydrogel biomedical materials of the 3rd example and the 4th example is similar to the crosslink time of the hydrogel compositions of the 1st example and the 2nd example, which means the additive has little effect on the crosslink rate of the hydrogel biomedical material.

Figure 10:
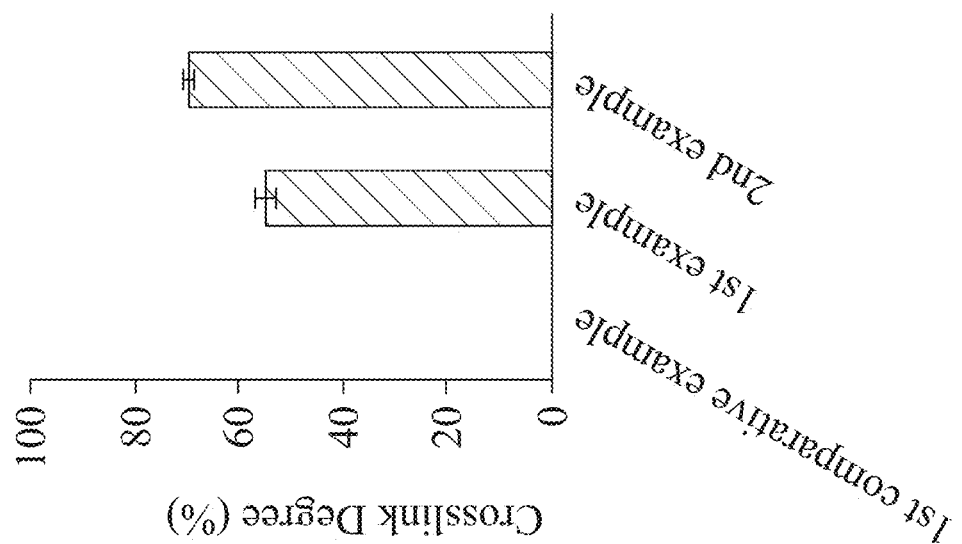
FIG. 10 is an analysis diagram of crosslink degree of the hydrogel compositions of the 1st comparative example, the 1st example and the 2nd example.

Furthermore, please refer to FIG. 10, which is an analysis diagram of crosslink degree of the hydrogel compositions of the 1st comparative example, the 1st example and the 2nd example. In FIG. 10, when the crosslink degrees of the hydrogel compositions of the 1st example and the 2nd example are higher than 50%, the hydrogel composition of the 1st comparative example does not form gel, which means the gelation rate thereof is significantly lower than the 1st example and the 2nd example. Between the hydrogel compositions of the 1st example and the 2nd example, the crosslink rate of the hydrogel composition of the 2nd example is highest.

In this regard, highly biocompatible materials such as gelatin, alginic acid, transglutaminase and hyaluronic acid are adopted as the materials of the hydrogel composition of the present disclosure. The hydrogel composition is able to carry the additive (such as the growth factor, the platelet-rich plasma, the platelet-rich fibrin and the antibiotic), and problems such as poor healing between bones and bone grafts, low osseointegration and osteomyelitis can be effectively improved.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A hydrogel composition, comprising:
a first deionized water;
a gel powder comprising gelatin and alginic acid;
a transglutaminase mixture; and
a hyaluronic acid powder;
wherein the first deionized water, the gel powder, the transglutaminase mixture and the hyaluronic acid powder are evenly mixed;
wherein based on the hydrogel composition being 100 wt %, the first deionized water is 95 wt % to 98.46 wt %, the gel powder is 1 wt % to 3 wt %, the transglutaminase mixture is 0.04 wt % to 0.15 wt %, and the hyaluronic acid powder is 0.5 wt % to 1.5 wt %.

2. The hydrogel composition of claim 1, wherein the transglutaminase mixture is made of a transglutaminase powder, a phosphate buffered saline, ethylenediaminetetraacetic acid and a second deionized water through a freeze-drying process.

3. A hydrogel biomedical material, comprising:
the hydrogel composition of claim 1; and
an additive, wherein the additive and the hydrogel composition are evenly mixed, and the additive is selected from the group consisting of a growth factor, a platelet-rich plasma, a platelet-rich fibrin and an antibiotic.

* * * * *